United States Patent
Chen et al.

(10) Patent No.: US 10,260,045 B2
(45) Date of Patent: Apr. 16, 2019

(54) USE OF COLLAGEN TYPE VII FOR MAINTAINING AND RE-INDUCING OSTEOGENIC ABILITIES OF MESENCHYMAL STEM CELLS

(75) Inventors: Mei Chen, Altadena, CA (US); David Woodley, Altadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/388,043

(22) PCT Filed: Jul. 30, 2010

(86) PCT No.: PCT/US2010/043997
§ 371 (c)(1),
(2), (4) Date: Jul. 30, 2012

(87) PCT Pub. No.: WO2011/014824
PCT Pub. Date: Feb. 3, 2011

(65) Prior Publication Data
US 2012/0308537 A1    Dec. 6, 2012

Related U.S. Application Data (60) Provisional application No. 61/230,600, filed on Jul. 31, 2009.

(51) Int. Cl.
*A61K 48/00* (2006.01)
*C12N 5/077* (2010.01)

(52) U.S. Cl.
CPC ...... *C12N 5/0654* (2013.01); *C12N 2501/155* (2013.01); *C12N 2501/70* (2013.01); *C12N 2501/998* (2013.01)

(58) Field of Classification Search
None
See application file for complete search history.

(56) References Cited

U.S. PATENT DOCUMENTS 6,541,024 B1 * 4/2003 Kadiyala et al. ............ 424/426

OTHER PUBLICATIONS

Chen et al., Experimental Cell Research, 1999, 249: 231-239.*
Klees et al., Mol Biol Cell, 2005, 16: 881-890.*
Salasznyk et al., Exp Cell Res, 2007, 313: 1-31.*
Pochampally et al., Gene Therapy, 2005, 12: 1119-1125.*
Longurst et al., Cell. Mol. Life Sci., 1998, 54: 514-526; Abstract.*
Maniatopoulos et al., Cell Tissue Res., 1988, 254: 317-330.*
Cassiede et al., J. Bone Miner. Res., 1996, 11: 1264-1273.*
Jaiswal et al., J. Biol. Chem., 2000, 275: 9645-9652.*
Schlaepfer et al., Progress in Biophysics & Molecular Biology, 1999, 71: 435-478.*
Guan, Matrix Biology, 1997, 16: 195-200.*
Hill et al., Developmental Cell, 2005, 8: 727-738.*
Caplan, Tissue Engineering, 2005, 11: 1198-1211.*
Catherine D. Reyes et al., "$\alpha_2\beta_1$ Integrin-specific collagen-mimetic surface supporting osteoblastic differentiation", Journal of Biomedical Maerials Research, vol. 69A, No. 4, Jun. 15, 2004, pp. 591-600.
Mizuno Morimichi et al., "Osteoblast-related gene expression of bone marrow cells during the osteoblastic differentiation induced by type I collagen", Journal of Biochemistry, vol. 129, No. 1, Jan. 2001, pp. 133-138.
Hulmes D.J.S., "Collagen Diversity, Synthesis and Assembly", Jan. 1, 2008, Collagen: Structure and Mechanics, pp. 15-47.
Jyrki Haino, "The Collagen Family Members as Cell Adhesion Proteins", Bioessays, Cambridge, vol. 29, No. 10, Oct. 1, 2007, pp. 1001-1010.
Roman M. Salasznyk et al,; Focal adhesion kinase signaling pathways regulate the osteogenic differentiation of human mesenchymal stem cells; Experimental Cell Research, 2007, vol. 313, No. 1, p. 22-37.
Japanese language Office Action dated Nov. 25, 2014 and its English language translation issued in corresponding Japanese application 2015-523105.
Hennessy et al., "The effect of collagen I mimetic peptides on mesenchymal stem cell adhesion and differentiation, and on bone formation at hydroxyapatite surfaces," NIH Public Access, Biomaterials. Apr. 2009 ; 30(10): 1898-1909. doi:10.1016/j.biomaterials.2008.12.053.
Official EPO Communication [Communication pursuant to Article 94(3) EPC] dated Jan. 16, 2017 issued in corresponding European Patent Application No. 10 739 816.6.

(Continued)

*Primary Examiner* — Ileana Popa
(74) *Attorney, Agent, or Firm* — DLA Piper LLP (US)

(57) ABSTRACT

This invention provides methods of inducing and maintaining osteogenic potential in mesenchymal stem cells and compositions for doing the same. The compositions this invention comprise collagen 7 (C7), the NC1 domain of C7, or the 27 kD fragment of C7. Also provided are methods for treating bone diseases and correcting bone defects by applying compositions of this invention or by first priming ex vivo mesenchymal stem cells with compositions of this invention and then applying the primed mesenchymal stem cells to the patient. The invention further provides a mesenchymal stem cell osteogenesis induction kit.

12 Claims, 11 Drawing Sheets

(56) References Cited

OTHER PUBLICATIONS

Chen, Mei, et al., "Interactions of the Amino-terminal Noncollagenous (NC1) Domain of Type VII Collagen with Extracellular Matrix Components. A Potential Role in Epidermal-Dermal Adherence in Human Skin", Journal of Biological Chemistry, vol. 272, No. 23, Jun. 6, 1997 (Jun. 6, 1997), pp. 14516-14522, XP055259075, US, ISSN: 0021-9258, DOI: 10.1074/jbc.272.23.14516.

Chen, Mei, et al., "The Cartilage Matrix Protein Subdomain of Type VII Collagen is Pathogenic of Epidermolysis Bullosa Acquisita", American Journal of Pathology., vol. 170, No. 6, Jun. 1, 2007 (Jun. 1, 2007), pp. 2009-2018, XP055334208, US, ISSN: 0002-9440, DOI: 10.2353/ajpath.2007.061212.

\* cited by examiner

USE OF COLLAGEN TYPE VII FOR MAINTAINING AND RE-INDUCING OSTEOGENIC ABILITIES OF MESENCHYMAL STEM CELLS

CROSS-REFERENCE TO RELATED APPLICATIONS

This application claims the benefit of U.S. Provisional Application No. 61/230,600, file on Jul. 31, 2009. The above application(s) is hereby incorporated herein by reference.

STATEMENT REGARDING FEDERALLY SPONSORED RESEARCH OR DEVELOPMENT

This invention was made with government support under Contract Nos. RO1 AR4798I and RO1 AR33625 awarded by the National Institute of Health. The government has certain rights in the invention.

FIELD OF THE INVENTION

The present invention relates in general to osteogenic potentiation. More specifically, the invention provides methods and compositions that are useful for maintaining and enhancing osteogenic potential of mesenchymal stem cells.

BACKGROUND OF THE INVENTION

Bone undergoes a continual remodeling process that requires the coordinated activity of two types of cells. Osteoclasts break down the bone matrix while osteoblasts deposit collagen, calcium, and phosphorous and other minerals to form new bone. The balance between the activity of osteoclasts and osteoblasts determines the mass and density of the bone. Many diseases of bone including osteoporosis, a common age-related phenomenon in post-menopausal women in which the bone mass has been greatly reduced, and osteogenesis imperfecta, also known as brittle-bone disease, are likely caused by the misregulation of osteoblasts and osteoclasts.

According to National Osteoporosis Foundation, osteoporosis alone currently affects about 44 million Americans. In addition, almost 34 million Americans are estimated to have low bone mass, placing them at increased risk for osteoporosis. By 2025, the annual direct costs of treating osteoporosis fractures in the US are estimated at $25 billion per year. Therefore, understanding the molecular mechanisms that underlie osteogenesis, the process by which new bone is formed, is of critical importance to improving the tools and methods for treating bone related diseases.

In this respect, stem cell technology, particularly mesenchymal stem cells (MSCs), offers an attractive sources of osteoblasts for tissue culture studies and for the biochemical dissection of the earliest steps involved in osteoblast cell determination. MSCs have the capacity for self-renewal and for differentiating into a variety of cells and tissues. Because of their multipotency, ease of isolation and culture, and immunosuppressive properties, these cells are also an attractive therapeutic tool for regenerative medicine. Given that autologous cells may be used for the eventual therapies, MSCs are particularly attractive in the context of bone and cartilage repair as well as other reconstructive applications. Clinical trials of MSC-based therapies are already underway for a number of diseases, including osteogenesis imperfecta, mucopolysaccharidoses, graft-versus-host disease, and myocardial infarction.

However, progress in MSC-based cell therapy for skeletal defects has been hindered by the MSCs' limited cell life-span and the fact that they progressively lose their osteogenic potential during ex vivo expansion. Further, the complexity of the signaling pathways that promote MSCs towards osteogenic differentiation poses significant challenges for in vivo application of MSCs. For example, the canonical Wnt-beta cantenin, bone morphogenetic protein (BMP), and extracellular matrix (ECM)-mediated Ras-Erk signally pathways have all been implicated in playing a critical role in the differentiation of MSCs to osteoblasts and in bone formation, but there is still no consensus as to how they work together in vivo. Thus, precise manipulation of MSCs in terms of inducing and stopping their osteogenic potential has been difficult.

To induce osteogenicity in MSCs, a number of ECM factors such as collagen type I and vitronectin, have been found to be effective. It has been reported that the greatest osteogenic differentiation occurred in MSCs plated on vitronectin and collagen type I and almost no differentiation took place on fibronectin or uncoated plates. Although it has been accepted that proteins and growth factors present in the ECM can drive stem cell differentiation by regulating gene expression, the sheer number of factors that exist in the ECM and the vast variety of signaling pathways interacting with each other render it virtually impossible to predict a priori the effects of any particular ECM factors. Studies have shown that ECM elements normally found in bone—such as laminin-1, fibronectin, and collagen 1—may have a defining effect on the differentiation of bone marrow progenitors. However, knowledge of the effects of these ECM elements is far from complete.

To advance the field of MSC-based therapy for bone or cartilage damages, more research tools and therapeutic agents capable of inducing and maintaining osteogenicity of MSCs are needed.

SUMMARY OF THE INVENTION

In light of the above mentioned unmet needs in the art, it is an object of the invention to provide a simple method for inducing and maintaining the osteogenic potential of MSCs.

It is also an object of this invention to provide reagents and research tools for inducing and maintaining the osteogenic potential of MSCs.

These and other objects of the invention are met by the inventors unexpected discovery that type VII collagen (C7), the NC1 domain of C7, and the CMP subdomain of C7 are all capable of inducing and maintaining the osteogenic potential of MSCs.

Figure 1:
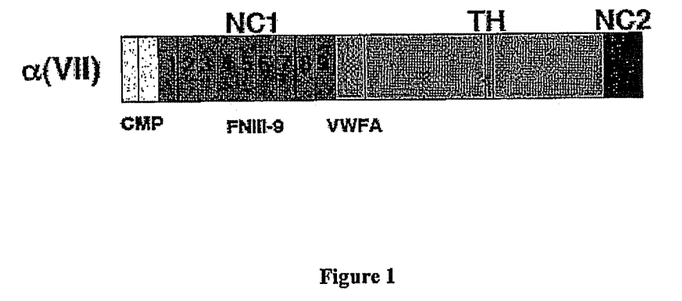
FIG. 1 shows a schematics representation of the structure of C7.

C7 is the major component of anchoring fibrils which are attachment structures in the cutaneous basement membrane zone (BMZ) that play a major role in epidermal-dermal adherence. Thus, C7 is an important factor in skin formation. FIG. 1 shows a schematic representation of C7's structure.

Because of the critical role that C7 plays in epidermal-dermal adherence, its connection to bone formation is quite unexpected. While not intending to be bound by any particular theory, the inventors observed that children with RDEB (an inherited skin disorder) also develop bone related diseases, and therefore hypothesized that skeletal defects found in most DEB patients may also be due to the absence of C7. Through extensive experimentation, the inventors have demonstrated that C7, the NC1 domain of C7, and the CMP subdomain of C7 are capable of inducing and maintaining the osteogenicity of MSCs.

Based on this unexpected discovery, the inventors have devised methods and compositions for inducing and maintaining osteogenicity in MSCs.

In one aspect, the invention provides a method for inducing and maintaining osteogenic potential hi MSCs. Embodiments in accordance with this aspect of the invention will generally include the steps of providing MSCs with an effective amount of an osteoinductive agent selected from the group consisting of C7, the NC1 domain of C7, and the CMP subdomain of the C7.

In another aspect, the invention provides a method of repairing a damaged bone or cartilage. Embodiments in accordance with this aspect of the invention will generally have the steps of applying MSCs to a damaged site in a bone or cartilage; and providing the MSCs with an effective amount of an osteogenic inducing agent selected from the group consisting of C7, the NC1 domain of C7, and the CMP subdomain of C7.

In a further aspect, the invention provides a method for manufacturing bone or cartilage material. Embodiments in accordance with this aspect of the invention will generally have the steps of growing MSCs in a suitable growth medium; providing an effective amount of osteoinductive agent to the MSCs to induce osteogenicity in the MSCs; and allowing the MSCs to grow into bone or cartilage. The osteoinductive agent is one selected from the group consisting of C7, the NC1 domain of C7, and the CMP subdomain of C7.

In a still further aspect, the invention provides a composition useful for inducing and maintaining osteogenic potential of MSCs. Embodiments in accordance with this aspect of the invention generally include an osteoinductive agent selected from the group consisting of C7, the NC1 domain of C7, and the CMP subdomain of C7.

In yet another aspect, the invention provides a MSC osteogensis induction kit. Embodiments in accordance with this aspect of the invention will generally include an osteoinductive agent selected from the group consisting of C7, the NC1 domain of C7, and the CMP subdomain of C7.

Because C7 is a naturally occurring protein, methods and compositions of this invention will enjoy the advantage of being readily compatible with host organisms. Thus, unlike methods based on high dosage of growth factors to stimulate bone growth, methods and compositions of this invention present lower risks for undesirable side-effects and are relatively inexpensive to implement.

Other aspects and advantages of the invention will be apparent from the following description and the appended claims.

DETAILED DESCRIPTION

The present invention will now be described in detail by referring to specific embodiments as illustrated in the accompanying figures.

Structurally, type VII collagen consists of three identical alpha chains which form a homotrimer. These align to form antiparallel dimers, which laterally aggregate to form anchoring fibrils.

As shown in FIG. 1, each alpha chain is composed of a central triple helical domain flanked by a large noncollagenous domain, NC1, at the N-terminal, and a smaller NC2, at the C-terminal. The NC1 domain has sub-modules with homology to multiple adhesive proteins including segments with homology to cartilage matrix protein (CMP), nine consecutive fibronectin type III-like repeats (FNIII), and the A domain of von-Willebrand factor (VWF-A).

As used herein, the term C7 refers to both native and recombinant C7 (the full-length sequence and structure of C7 has been fully described by Christiano, A. M., Greenspan, D. S., Lee, S., and Uitto, J. (1994) *J. Biol. Chem.* 269, 20256-20262, the entire content of which is incorporated herein by reference).

The term NC1 domain refers to the first 1254 amino acids of C7.

The term CMP domain refers to the first 227 amino acids of C7.

The inventors have discovered that any fragment of C7 containing the CMP subdomain will generally be effective in inducing and maintaining the osteogenicity of MSCs, albeit to varying degrees. Full length C7 down to NC1 is relatively effective whereas the CMP subdomain is less so.

In one aspect, the invention provides a method for inducing and maintaining osteogenic potential in MSCs. Embodiments in accordance with this aspect of the invention will generally include the steps of providing MSCs with an effective amount of an osteoinductive agent selected from the group consisting of C7, the NC1 domain of C7, and the CMP subdomain of the C7.

The MSCs should be placed in a suitable environment such as an osteogenic medium. Exemplary osteogenic induction medium may include α-MEM containing 16.7% Premium FBS (Atlanta Biologicals Cat# S11550), 2 mM L-Glutamine, 20 mM β-glycerophophate, $10^{-7}$ M or 100 nM Dexamethasone, and 100 µg/ml freshly prepared L-ascorbic acid.

In some embodiments, the osteoinductive agent is provided exogenously. Exogenous application of the osteoinductive agent may be accomplished by simply contacting the cells with the agent. For example, the agent may be provided in a suitable solution medium and delivered the Petri dish containing the MSCs. Any other commonly known methods of exogenously supplying the agent may also be used.

In other embodiments, the osteoinductive agent is provided endogenously via an expression vector configured to over-express the osteoinductive agent. In still some embodiments, the vector may be further configured to express the induction agent only when a trigger signal is present so that timing of the expression may be controlled.

The source and passage of the MSCs are not particularly limited. MSCs may be obtained from early passages or late passages during cell culture expansion. The osteoinductive agents of this invention are capable of inducing osteogenicity even in late passage cells. For the purpose of this invention, early passage refers to passage 2 to passage 5. Late passage refers to passage 8 to passage 12.

Effective amount of C7 added to the medium is generally in the range of 0.5 µg-1 µg/ml added to the osteogenic induction medium.

The design of vectors containing osteoinductive agents of this invention can be done with any vector design methods commonly known in the art.

In another aspect, the invention provides a method of repairing a damaged bone. Under permissive stimulation or an appropriate microenvironment, MSCs undergo osteogenic differentiation through a well-defined pathway, acquiring osteoblastic markers and secreting extracellular matrix and calcium.

Embodiments in accordance with this aspect of the invention will generally have the steps of applying MSCs to a damaged site in a bone or cartilage; and providing the MSCs with an effective amount of an osteogenic inducing agent selected from the group consisting of C7, the NC1 domain of C7, and the CMP subdomain of C7. Methods of exogenously or endogenously supplying effective amounts of the osteoinductive agent are as described above.

When supplying the osteoinductive agent exogenously, it is preferred that the MSCs are treated with C7 or its subdomain NCI or CMP prior to applying the MSCs to the damage site.

In a further aspect, the invention provides a method for manufacturing bone or cartilage material. Embodiments in accordance with this aspect of the invention will generally have the steps of growing MSCs in a suitable growth medium; providing an effective amount of osteoinductive agent to the MSCs to induce osteogenicity in the MSCs; and allowing the MSCs to grow into bone or cartilage. The osteoinductive agent is one selected from the group consisting of C7, the NC1 domain of C7, and the CMP subdomain of C7.

In a still further aspect, the invention provides a composition useful for inducing and maintaining the osteogenic potential of MSCs. Embodiments in accordance with this aspect of the invention generally include an osteoinductive agent selected from the group consisting of C7, the NC1 domain of C7, and the CMP subdomain of C7.

In yet another aspect, the invention provides a MSC osteogensis induction kit. Embodiments in accordance with this aspect of the invention will generally include an osteoinductive agent selected from the group consisting of C7, the NC1 domain of C7, and the CMP subdomain of C7.

The following experiments further demonstrates the various aspects of this invention.

EXPERIMENTS

C7 Significantly Enhances the Osteogenic Potential of Human MSCs

Figure 2:
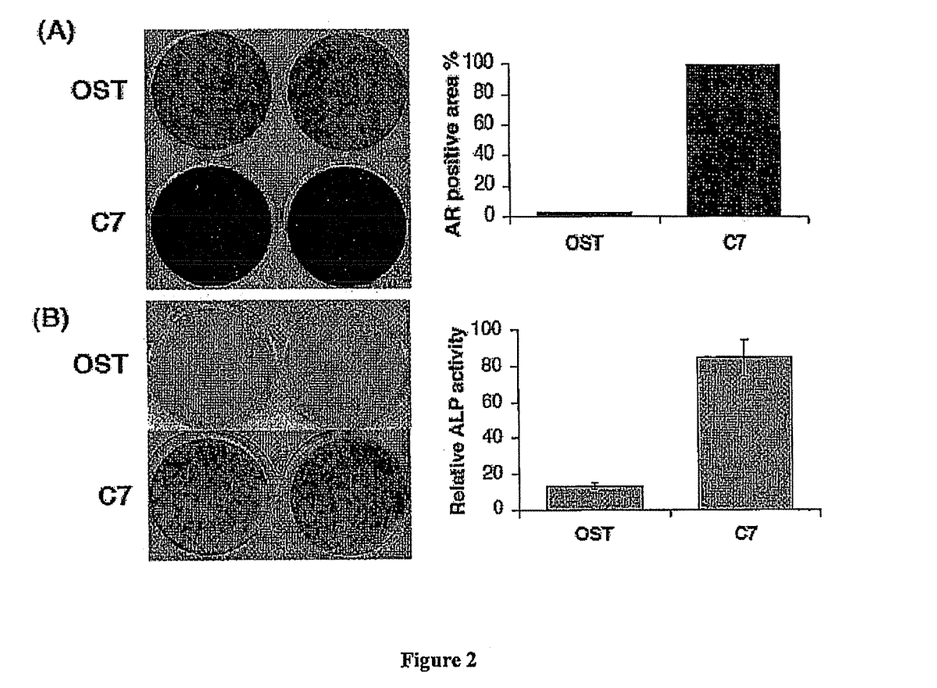
FIG. 2 shows the result of C7 osteoinduction in human MSCs.

FIG. 2 shows the result of C7 osteoinduction in human MSCs. FIG. 2A shows scanned images of Alizarin red (AR) staining in MSCs (left) and their quantification (right). Alizarin red (AR) staining is normally used to determine the calcium accumulation and mineralization that are associated with bone formation. Cells in the tissue culture dishes labeled C7 were incubated with osteogenic induction medium containing 1.0 µg/ml of C7. Cells in the tissue culture dishes labelled OST were incubated with osteogenic induction medium alone (controls). The results show the MSCs after 21 days of incubation in an osteogenic medium.

FIG. 2B shows scanned images of alkaline phosphotase (ALP) staining (left) and their quantification (right). ALP measures the expression of a key marker enzyme that is needed for bone formation. The tissue culture dishes labeled C7 were treated with 1.0 µg/ml C7 whereas dishes label OST were the controls. The cells were incubated in an osteogenic medium for 14 days.

Quantification of the stained images represents mean values+/−standard deviation from experiments performed in triplicate. As demonstrated herein, C7 treatment significantly enhances osteogenic potential of human MSCs as measured by increased AZ and ALP activities.

Figure 3:
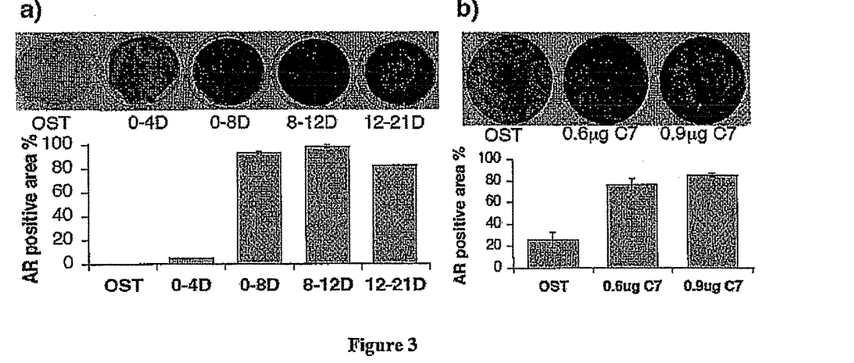
FIG. 3 shows the dose response and time course of C7 treatment.

C7 Only Needs to be Added During Days 8-12 at 0.6 µg/ml to Achieve Optimal Osteogenic Induction FIG. 3 shows the dose response and time course of C7 treatment. FIG. 3A is the scanned image of Alizarin red staining (top) and its quantification (bottom). The image shows MSCs treated with 1.0 µg/ml of C7 for discrete time periods in the presence of an osteogenic medium for 21 days.

FIG. 3B is the scanned image of Alizarin red staining (top) and its quantification (bottom). The image shows MSCs treated with increasing doses of C7 (0.6 µg/ml and 0.9 µg/ml) in the presence of an osteogenic medium for 21 days. The results represent mean values+/−standard deviation from experiments performed in triplicates. Note that MSCs only need to be exposed to 0.6 µg/ml of C7 during days 8-12 to attain optimal osteogenic induction.

For these experiments, plated MSCs were plated at $3 \times 10^5$/per well on 6-well plates in MSC growth medium containing α-MEM containing 16.7% Premium FBS (Atlanta Biologicals Cat# S11550), and 2 mM L-Glutamine. After the cells reached 70% confluency, the medium was changed to osteogenic induction medium with or without 0.6 µg/ml C7 added at the time period indicated above.

NC1 Domain of C7 is Sufficient for Enhancing MSC Osteogenic Potential

As shown in FIG. 1, the full-length C7 contains within it several domains, including a homologue of cartilage matrix protein (CMP), 9 fibronectin type III-like repeats (FNIII), and a region homologous to the A domain of von Willebrand factor (VWF-A). In this experiment, the osteoinductive capability of NC1 was tested.

Figure 4:
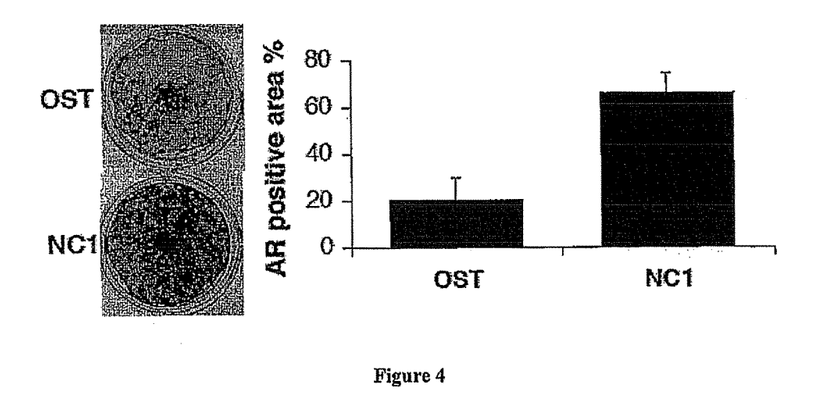
FIG. 4 shows that the NC1 domain of C7 is sufficient for osteoinduction in human MSCs.

The result of the experiment is shown in FIG. 4. Scanned image of Alizarin red staining (left) and its quantification are shown in the Figure. Here the MSCs were treated with 4 µg/ml of NC1 for 21 days in an osteogenic medium. Results represent mean values+/−standard deviation from experiments performed in triplicates.

In general, NC1 also enhances the osteogenic potential of MSC although with less efficacy compared with full length C7. Further, the concentration of NC1 (4 µg/ml) needed for enhancing MSC osteogenic potential is higher than that required for full length C7.

Figure 5:
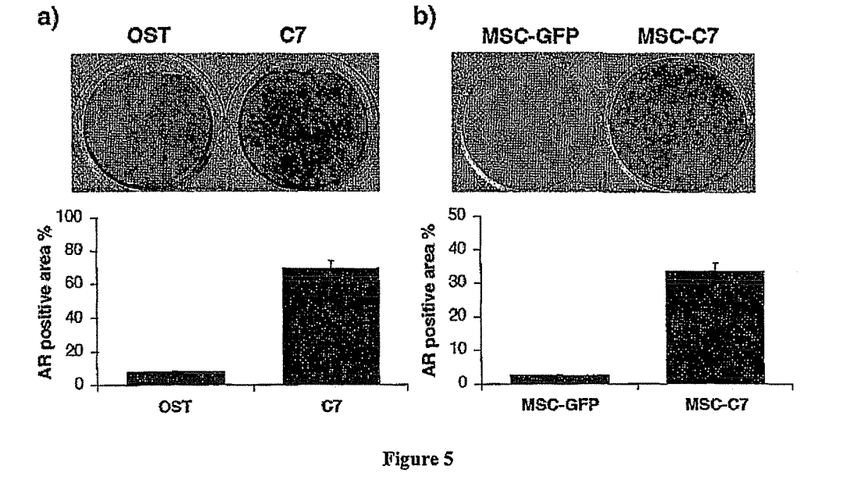
FIG. 5 shows that C7 is capable of sustaining and enhancing osteogenic potential in late passage MSCs.

Overexpression or Exogenously Added C7 in Non-Osteogenic Late Passage MSCs Re-Induces their Osteogenic Potential FIG. 5 shows that C7 is capable of sustaining and enhancing the osteogenic potential in late passage MSCs. FIG. 5A is the scanned image of Alizarin red staining (top) and its quantification (bottom). Late passage MSCs (passage 8)

were treated with 1.0 µg/ml of C7 in the presence of an osteogenic medium for 21 days.

FIG. 5B is the scanned image of Alizarin red staining (top) and its quantification (bottom). Late passage MSCs infected with lentiviral vectors expressing either green fluorescence protein (GFP) or C7 were subjected to osteogenic medium for 21 days. Results represent mean values+/−standard deviation from experiments performed in triplicates.

This experiment demonstrated that exogenous addition or overexpression of C7 in late passage MSCs are both capable of restoring the MSCs' osteogenic potential.

For these experiments, MSCs from passage 3 were infected with lentiviral vectors expressing either GFP or C7 and cultured for an additional 7 passages. Then infected MSCs (passage 10) were plated at 6 well-plates and then subjected to osteogenic induction medium.

C7 Upregulates the Expression of Osteoblast Markers and Dramatically Enhances the Expression of the Master Bone Regulator, Runx2

Figure 6:
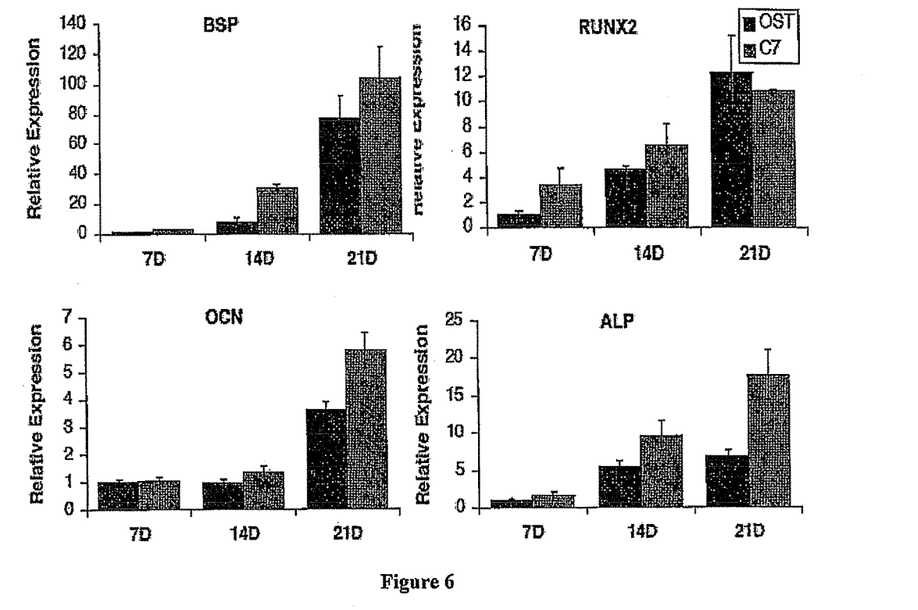
FIG. 6 shows the result of real-time PCR analysis of osteogenic-specific gene expression.

FIG. 6 shows the result of Real-Time PCR (RT-PCR) analysis of osteogenic-specific gene expression. In this experiment, MSCs were cultured in 6-well plates in growth medium until they reached confluence. Then, they were switched to osteogenic medium. Respective wells were treated with 1.0 µg/ml C7 until the indicated harvest days. Equal amounts of RNA were reverse transcribed and the mRNA levels of the indicated genes were analyzed using SYBR green master mix and primers for alkaline phosphotase (ALP), Runx2, bone sialoprotein (BSP), and osteocalcin (OCN). Data were normalized to house keeping gene GAPDH and expressed as fold-changes relative to 7D untreated cells. Results represent the mean+/−standard deviation of duplicate experiments with PCR performed in triplicates.

This experiment clearly demonstrated that C7 upregulates both early osteogenic markers (ALP, BSP, Runx2) and the late marker, OCN.

Figure 7:
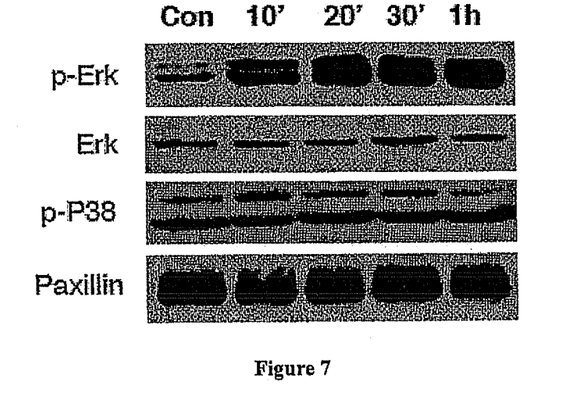
FIG. 7 shows the experimental results demonstrating that C7 activates the Ras-Erk signaling pathway.

C7 Specifically Activates the Ras-ERK Pathway in MSCs Under Osteogenic Conditions FIG. 7 shows that osteoinduction by C7 activates the Ras-ERK signaling pathway. In this experiment, cells were serum starved for 48 hours and then stimulated with osteogenic medium in the absence or presence of 1.0 µg/ml C7. Cellular extracts were prepared at the times indicated and then subjected to immunoblot analysis with antibodies shown above. Total ERK and paxillin are included to indicate equal protein loading.

It should be noted that C7 stimulated the phosphorylation of ERK (p-Erk), but not p-P38.

As shown in FIG. 7, C7 treatment increased production of p-ERK as early as 10 minutes, which was sustained up to 1 hour. In contrast, the levels of ERK and p-P38 remained unchanged. It should be pointed out that phosphorylation of ERK (p-ERK) initiates the Ras-ERK signaling pathway.

C7-Mediated Osteogenic Enhancement of MSCs can be Abolished by an ERK Specific Inhibitor U0126

Figure 8:
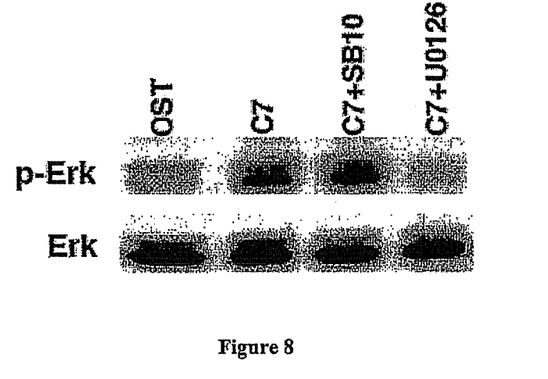
FIG. 8 shows experimental result demonstrating that C7-activated Erk response is abolished by the Erk-specific inhibitor U0126.

FIG. 8 shows ERK activation by C7 can be abolished by ERK-specific inhibitor. In this experiment, cells were pre-treated with the respective inhibitor for 1 hour before addition of 1.0 µg/ml C7. Proteins were collected after 1 hour and subjected to immunoblot analysis with antibody as indicated in the figure. Regular ERK is included as a control for equal protein loading.

ERK-Specific Inhibitor U0126 Abrogated C7-Mediated Induction of p-ERK, but a Non-Specific P38 Inhibitor, SB10, had No Effect.

FIG. 9A is a scanned image of Alizarin staining (left) and its quantification (right). Here the MSCs were treated with 1.0 µg/ml C7 or 1.0 µg/ml C7 and 15 µM U0126 in the presence of an osteogenic medium for 21 days. In FIG. 9B, MSCs were cultured as in FIG. 9A. RNAs were collected after 14 days and subjected to RT-PCR analysis for early osteogenic gene markers. Results for staining represent mean values+/−standard deviation from experiments performed in quadruplicate. RT-PCR results represented the mean+/−standard deviation of duplicate experiments with PCR performed in triplicates. The ERR-specific inhibitor abolished C7-induced calcium deposition and expression of early osteogenic gene markers.

Thus, these experiments demonstrate that ERK-specific inhibitor is capable of abrogating the osteoinductive effect of C7.

Figure 9:
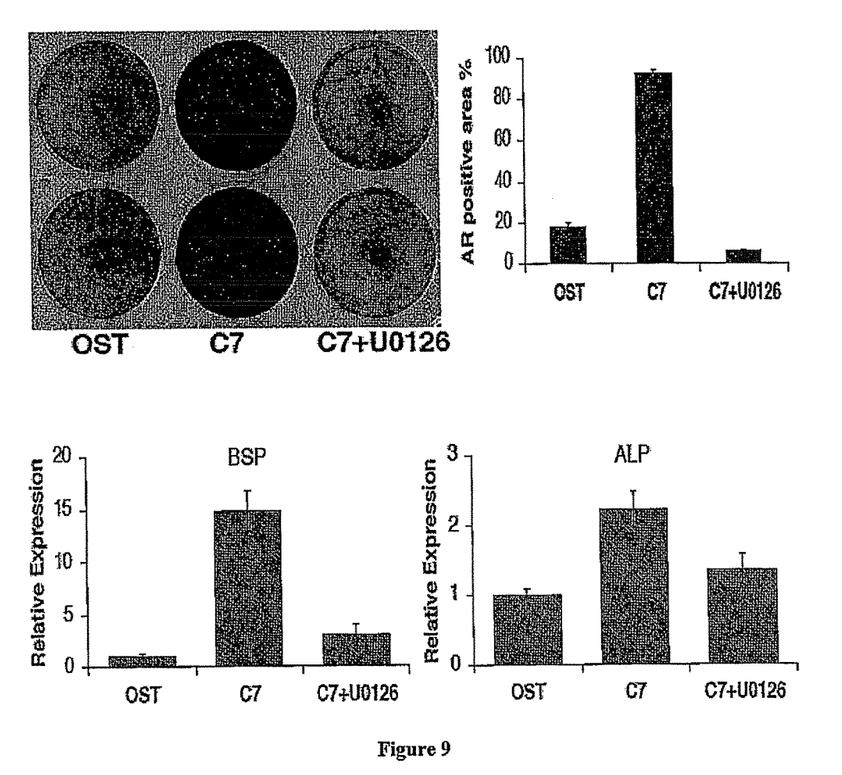
FIG. 9 shows the effect of ERK-specific inhibitor on C7-induced osteogenic differentiation.

As show in FIG. 9, incubation of MSC with a specific ERR inhibitor, UO126, abolished the C7-mediated osteogenic induction. These were demonstrated by reduced AR staining in FIG. 9A and mRNA expression of BSP and ALP in FIG. 9B, two markers associated with bone formation.

Low Dose of C7 (10 µg) Significantly Enhances BMP-2 Mediated Bone Induction

This example demonstrates that C7 is also capable of enhancing BMP-2 mediated bone induction in vivo.

High concentration of BMP-2 was used as positive control. The negative control was carrier only, which consisted of collagen sponge (bovine). The samples were administered to rat via intramuscular implantation on ectopic sites. The experiment lasted for 4 weeks. Two different preparations (C7 and C7') were tested. The test dosages were: 10, 20 and 40 µg.

The results were analyzed by alkaline phosphotase assay (ALP) and histology for bone formation. It was found that C7 and C7' at low dosages (10 µg) were able to significantly enhance BMP-2-mediated bone induction. Table 1 below shows the result for ALP analysis. Table 2 shows the histology analysis,

TABLE 1

ALP assay analysis of the effect of C7 and C7' on ectopic osteogenesis induction

| Histo ID | Sample name | C7 or C7' (µg) | BMP-2 (µg) | ALP | Protein | ALP/Pro | Note |
|---|---|---|---|---|---|---|---|
| 6630 | C7 0.5 ug/ul | 10 |  | 0.094 | 0.182 | 0.517 | Rat A |
| 6631 |  | 20 |  | 0.094 | 0.188 | 0.500 |  |
| 6632 |  | 40 |  | 0.092 | 0.253 | 0.364 |  |
| 6633 |  | 10 | 1 | 0.257 | 0.109 | 2.360 |  |
| 6634 |  | 20 | 1 | 0.384 | 0.203 | 1.893 |  |
| 6635 |  | 0 | 1 | 0.163 | 0.186 | 0.877 |  |
| 6636 | C7' 0.3 ug/ul | 10 |  | 0.093 | 0.114 | 0.816 | Rat B |
| 6637 |  | 20 |  | 0.091 | 0.174 | 0.522 |  |
| 6638 |  | 40 |  | 0.084 | 0.191 | 0.440 |  |
| 6639 |  | 10 | 1 | 0.202 | 0.119 | 1.700 |  |
| 6640 |  | 20 | 1 | 0.170 | 0.182 | 0.934 |  |
| 6641 |  | 0 | 3 | 0.476 | 0.133 | 3.571 |  |

TABLE 2

Histology analysis of the effect of C7 and C7' on ectopic osteogenesis induction

| Histo ID | Sample name | C7 or C7' (ug) | BMP-2 (ug) | Bone score | Note |
|---|---|---|---|---|---|
| 6630 | C7 0.5 ug/ul | 10 |  | 0 | Rat A |
| 6631 |  | 20 |  | 0 |  |

TABLE 2-continued

Histology analysis of the effect of C7 and C7' on ectopic osteogenesis induction

| Histo ID | Sample name | C7 or C7' (ug) | BMP-2 (ug) | Bone score | Note |
|---|---|---|---|---|---|
| 6632 | | 40 | | 0 | |
| 6633 | | 10 | 1 | 3 | |
| 6634 | | 20 | 1 | 0 | |
| 6635 | | 0 | 1 | 0 | |
| 6636 | C7' 0.3 ug/ul | 10 | | 0 | Rat B |
| 6637 | | 20 | | 0 | |
| 6638 | | 40 | | 0 | |
| 6639 | | 10 | 1 | 2 | |
| 6640 | | 20 | 1 | 0 | |
| 6641 | | 0 | 3 | 4 | |

Figure 10:
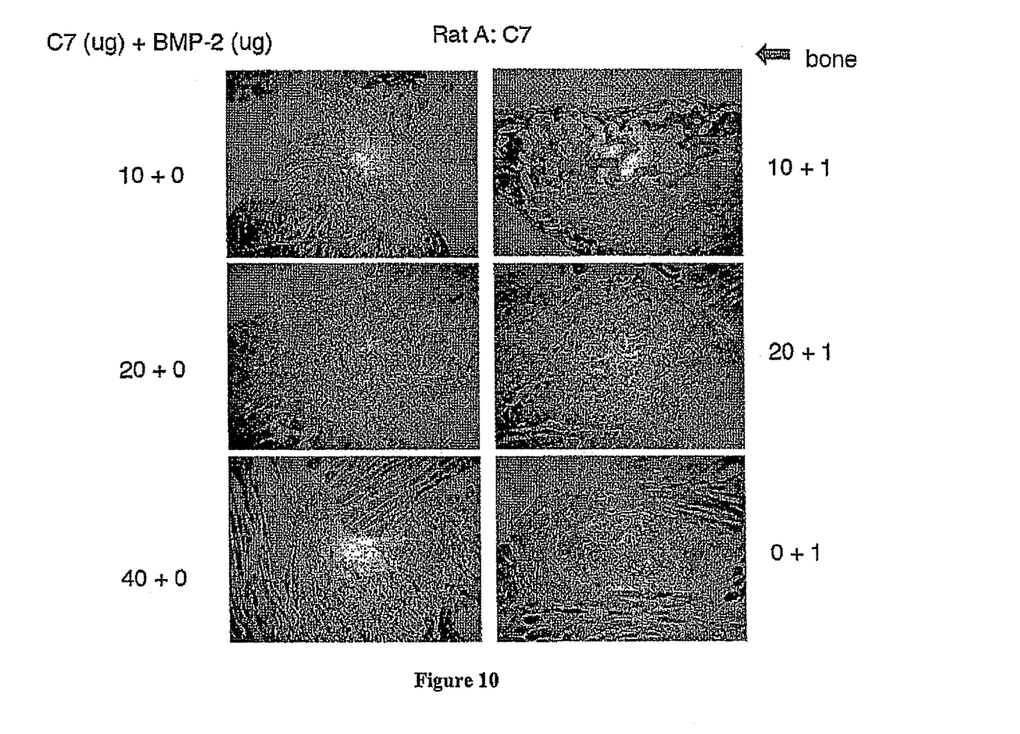
FIG. 10 shows an exemplary result of osteogenesis induction in a rat that received varying dosages of C7+BMP-2.
Figure 11:
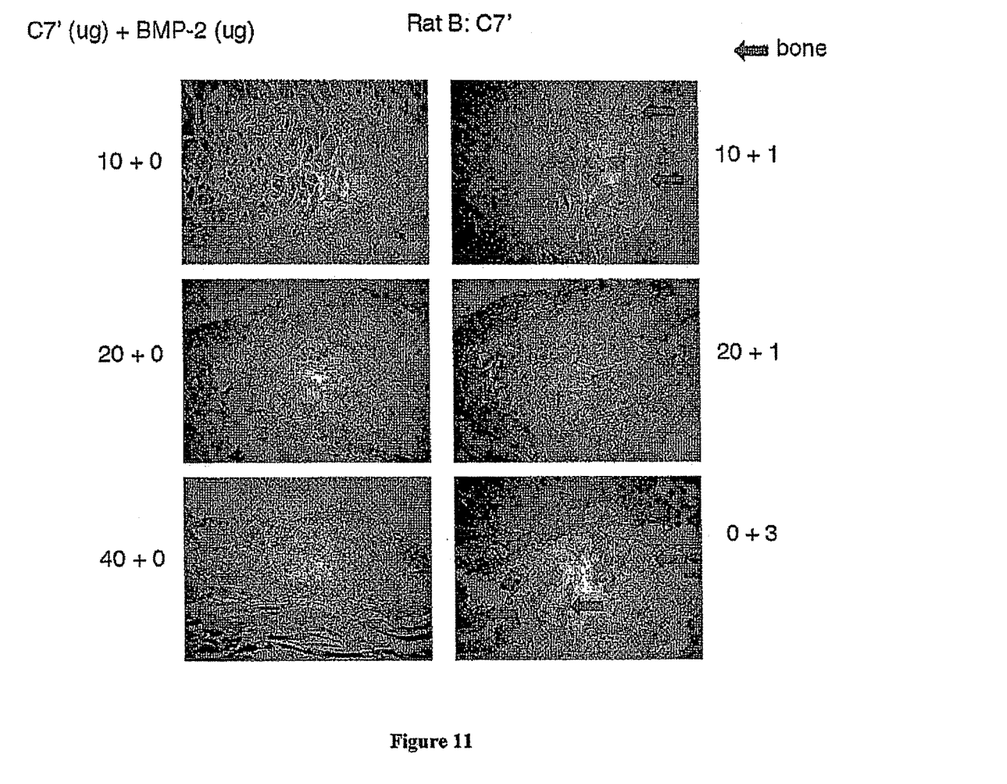
FIG. 11 shows an exemplary result of osteogenesis induction in a rat that received varying dosages of CT+BMP2.

FIG. 10 shows an exemplary result of osteogenesis induction in a rat that received varying dosages of C7+BMP-2. FIG. 11 shows an exemplary result of osteogenesis induction in a rat that received varying dosages of CT+BMP2.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. An in vitro method for inducing and maintaining osteogenic potential in mesenchymal stem cells, comprising:
   providing an effective amount of an osteoinductive agent to said mesenchymal stem cells in an osteogenic medium,
wherein said osteoinductive agent is the CMP subdomain of C7.

2. The method of claim 1, wherein said mesenchymal stem cells are one from passages P2-P5 during cell expansion.

3. The method of claim 1, wherein said mesenchymal stem cells are one from late passages during cell expansion.

4. The method of claim 1, wherein said osteoinductive agent is provided to the mesenchymal stem cells exogenously.

5. The method of claim 1, wherein said osteoinductive agent is provided endogenously via an expression vector configured to over-express said induction agent in the mesenchymal stem cells.

6. A method of repairing a damaged bone, comprising:
   applying mesenchymal stem cells to the damaged bone; and
   providing said mesenchymal stem cells with an effective amount of an osteoinductive agent to induce osteogenicity in the mesenchymal stem cells,
wherein said osteoinductive agent is the CMP subdomain of C7.

7. The method of claim 6, wherein said CMP subdomain of C7 is provided exogenously.

8. A method of repairing a damaged bone comprising:
   providing mesenchymal stem cells to the damaged bone, wherein the mesenchymal stem cells are genetically modified with an expression vector encoding the CMP subdomain of C7 and wherein the genetically modified mesenchymal stem cells overexpress the CMP of C7 thereby repairing the damaged bone.

9. An in vitro method for manufacturing bone material, comprising:
   growing mesenchymal stem cells in an osteogenic medium;
   providing an effective amount of osteoinductive agent to the mesenchymal stem cells to induce osteogenicity in the mesenchymal stem cells; and
   allowing the mesenchymal stem cells to form bone,
wherein said osteoinductive agent is the CMP subdomain of C7.

10. The method of claim 9, further comprising a step of abolishing osteogenicity in the mesenchymal stem cells by treating the cells with an Erk-specific inhibitor.

11. The method of claim 10, wherein said Erk-specific inhibitor is U0126.

12. A composition for inducing and maintaining osteogenic potential in mesenchymal stem cells, comprising:
   mesenchymal stem cells;
   an effective amount of the CMP subdomain of C7; and
   an osteogenic medium.

* * * * *

UNITED STATES PATENT AND TRADEMARK OFFICE
CERTIFICATE OF CORRECTION

PATENT NO. : 10,260,045 B2  
APPLICATION NO. : 13/388043  
DATED : April 16, 2019  
INVENTOR(S) : Chen et al.

Page 1 of 1

It is certified that error appears in the above-identified patent and that said Letters Patent is hereby corrected as shown below:

In the Specification

Column 1, Lines 16-19 Delete:
"This invention was made with government support under Contract Nos. RO1 AR4798I and RO1 AR33625 awarded by the National Institute of Health. The government has certain rights in the invention."

Insert:
--This invention was made with government support under Contract Nos. R01 AR047981 and R01 AR033625 awarded by the National Institutes of Health. The government has certain rights in the invention.--

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*